(12) United States Patent
East

(10) Patent No.: US 8,604,267 B2
(45) Date of Patent: Dec. 10, 2013

(54) DISPOSABLE NOSE PACK FOR NOSEBLEEDS

(75) Inventor: Merrie Kay East, Andover, KS (US)

(73) Assignee: Merrie K. East

( * ) Notice: Subject to any disclaimer, the term of this patent is extended or adjusted under 35 U.S.C. 154(b) by 565 days.

(21) Appl. No.: 12/157,299

(22) Filed: Jun. 9, 2008

(65) Prior Publication Data

US 2009/0306575 A1 Dec. 10, 2009

(51) Int. Cl.
*A61F 13/20* (2006.01)
*A61F 13/34* (2006.01)

(52) U.S. Cl.
USPC .......................................... 604/358; 604/11

(58) Field of Classification Search
USPC ................ 604/19; 128/898, 201.18, 207.13, 128/206.11
See application file for complete search history.

(56) References Cited

U.S. PATENT DOCUMENTS

| | | | |
|---|---|---|---|
| 592,659 A | 10/1897 | Miller et al. | |
| 1,042,624 A | 10/1912 | Wagoner | |
| 1,133,770 A | 3/1915 | Wedler | |
| 1,235,095 A | 7/1917 | Beck | |
| 1,887,526 A | 11/1932 | Spielberg et al. | |
| 2,691,985 A | 10/1954 | Newsom | |
| 3,038,214 A * | 6/1962 | Griswold et al. | 28/120 |
| 3,049,125 A | 8/1962 | Kriwkowitsch | |
| 3,570,494 A | 3/1971 | Gottschalk | |
| 3,618,607 A | 11/1971 | Ells et al. | |
| 3,850,176 A | 11/1974 | Gottschalk | |
| 4,030,504 A | 6/1977 | Doyle | |
| 4,568,326 A | 2/1986 | Rangaswamy | |
| 4,646,739 A | 3/1987 | Doyle | |
| 4,705,514 A * | 11/1987 | Barnard | 604/383 |
| 4,820,266 A * | 4/1989 | Berry | 604/11 |
| 4,895,559 A | 1/1990 | Shippert | |
| 4,952,204 A * | 8/1990 | Korteweg | 604/1 |
| 5,011,474 A | 4/1991 | Brennan | |
| 5,327,897 A | 7/1994 | Andresen | |
| 5,383,891 A * | 1/1995 | Walker | 606/196 |
| 5,531,703 A | 7/1996 | Skwarek et al. | |
| 5,568,808 A | 10/1996 | Rimdus | |
| 5,584,822 A * | 12/1996 | Lively et al. | 604/286 |
| 5,713,855 A | 2/1998 | Shippert | |
| 5,827,224 A | 10/1998 | Shippert | |
| 5,890,491 A | 4/1999 | Rimkus | |
| 5,891,123 A * | 4/1999 | Balzar | 604/385.18 |

(Continued)

*Primary Examiner* — Susan Su

(57) ABSTRACT

A cylindrical absorbent cotton nasal pack has a rounded tip for a patient's self application in controlling epistaxis. The pack comprises compressed absorbent cotton or cellulosic fiber in the shape of a bullet or capsule to prevent sticking to nasal wall and absorption of blood. One end has a rounded tip and the other end has a flat bottom section (optional dual rounded ends). The flat bottom section has a plastic coating or plastic sleeve made of polyurethane to help grip the nose pack, conceal the site of blood, prevent blood leakage, and prevent contact of blood when disposing of the nose pack. The nose pack is simply inserted with the cotton rounded side up into the bleeding nasal cavity while applying a gentle pushing force until pack is snug at top of nasal cavity. The constant pressure applied from the pack to the nostril wall assists in the coagulation process, which helps stop the nosebleed. The nose pack is sized to be placed within the nasal cavity upon occurrence of a nosebleed. When the nosebleed is ended, the nose pack may be removed by applying a gentle pulling force to the bottom of the nose pack to remove from nasal cavity. When removing the pack, blood clots that collected during the coagulation process will also naturally be released.

7 Claims, 1 Drawing Sheet

(56) References Cited

U.S. PATENT DOCUMENTS

| | | |
|---|---|---|
| 6,123,697 A | 9/2000 | Shippert |
| 6,216,694 B1 | 4/2001 | Chen |
| 6,517,509 B1 * | 2/2003 | Shippert .................. 604/11 |
| 6,559,352 B2 * | 5/2003 | Zadini et al. .................. 604/358 |
| 6,768,040 B1 * | 7/2004 | Sessions et al. ............... 602/56 |
| 7,294,138 B2 * | 11/2007 | Shippert ...................... 606/196 |
| 7,789,845 B1 * | 9/2010 | Meliti .............................. 604/1 |
| 2001/0001788 A1 * | 5/2001 | Satoh et al. .................... 514/25 |
| 2003/0167048 A1 | 9/2003 | Policappelli |
| 2005/0054967 A1 * | 3/2005 | Ashe et al. ...................... 604/2 |
| 2005/0288620 A1 * | 12/2005 | Shippert ...................... 604/11 |
| 2006/0036206 A1 | 2/2006 | Yokoyama et al. |
| 2006/0137069 A1 * | 6/2006 | Yang et al. ........................ 2/21 |

\* cited by examiner

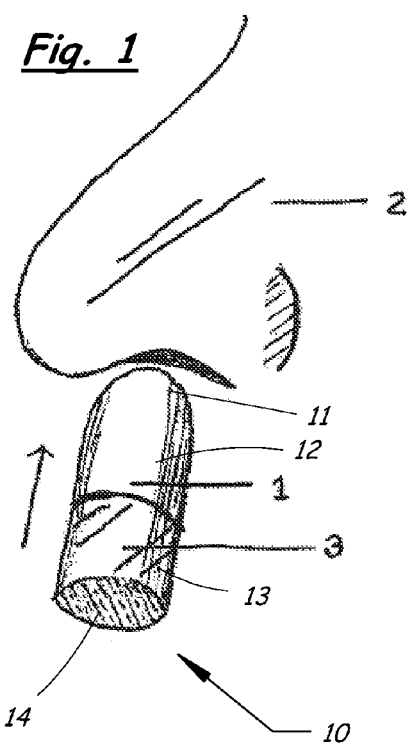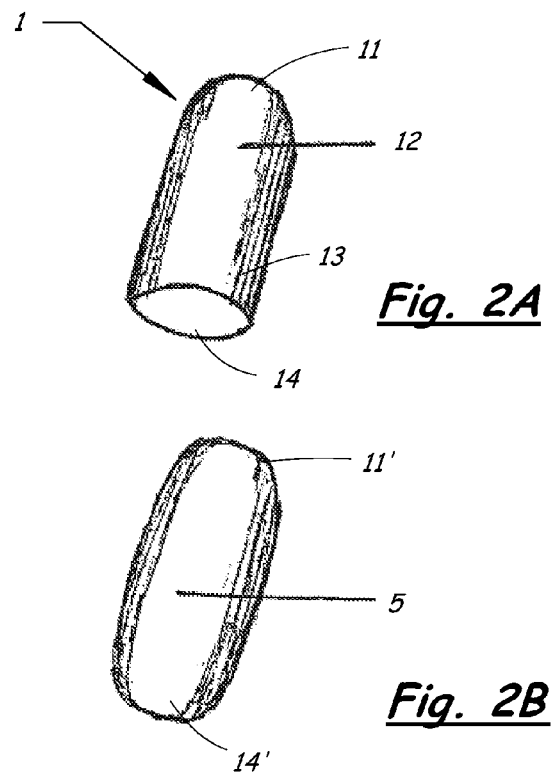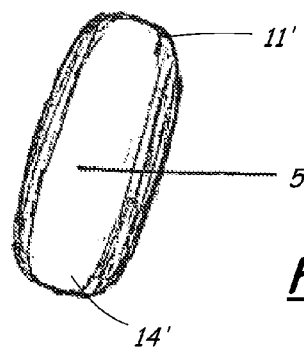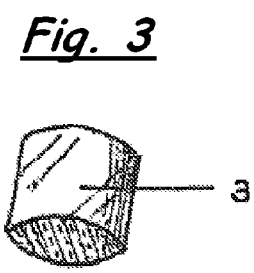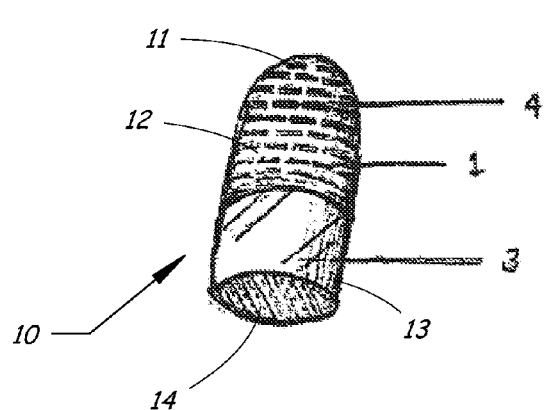

DISPOSABLE NOSE PACK FOR NOSEBLEEDS

BACKGROUND OF THE INVENTION

1. Field of the Invention

The present invention relates generally to disposable epistaxis treatments, which can be applied with ease by patient without medical assistance.

2. Description of Prior Art

Epistaxis, also known as "nosebleed," is a common problem. There are many causes for nosebleeds which can be propagated by excessive drying of nasal mucous membrane, trauma (physical damage), hypertension (high blood pressure), and sinusitis, among other disorders. Nosebleeds frequently occur at unpredictable times and can be dangerous if not controlled causing unconsciousness or even death. Because of the frequency, unpredictability and danger of nosebleeds, it is critical that treatment for nosebleeds be readily available, especially for those people with chronic nosebleeds. According to OSHA, there are regulations regarding contact of blood and many people are fearful that the blood may be contaminated with blood borne pathogens such as AIDS or HIV. Players in sporting events cannot continue playing if blood is seen by the referee, unless the nose bleed is "contained". This nose pack has a compacted design to help conceal the problem of a nosebleed thereby preventing embarrassment of messy blood. For these reasons, many attempts have been made to meet the need for a simple and ready to use treatment with the ability to conceal a nosebleed for epistaxis. All attempts in the prior art have failed to satisfactorily meet these needs. A satisfactory treatment would be non conspicuous, effective, easily disposable, convenient, cost effective and easy to apply, while not intimidating patients.

Field of Search

References Cited

US Patent Documents

| | | |
|---|---|---|
| 592659 | October 1897 | Miller et al. |
| 1042624 | October 1912 | Wagoner |
| 1133770 | March 1915 | Wedler |
| 1235095 | July 1917 | Beck |
| 1887526 | November 1932 | Spielberg et al. |
| 2691985 | October 1954 | Newsom |
| 3049125 | August 1962 | Kriwkowitsch |
| 3570494 | March 1971 | Gottschalk |
| 3618607 | October 1971 | Ells, et al |
| 3850176 | November 1974 | Gottschalk |
| 4030504 | June 1977 | Doyle |
| 4568326 | February 1986 | Rangaswamy |
| 4646739 | March 1987 | Doyle |
| 4705514 | November 1987 | Barnard |
| 4895559 | January 1990 | Shippert |
| 5011474 | April 1991 | Brennan |
| 5327897 | July 1994 | Andresen |
| 5383891 | January 1995 | Walker |
| 5568808 | October 1996 | Rimkus |
| 5584822 | December 1996 | Lively |
| 5713855 | February 1998 | Shippert |
| 5827224 | October 1998 | Shippert |
| 5890491 | April 1999 | Rimkus |
| 6123697 | September 2000 | Shippert |
| 6216694 | April 2001 | Chen |
| 5531703 | July 1996 | Skwarek |

US Patent Documents

| | | |
|---|---|---|
| 2003/0167048 | September 2003 | Policappelli |
| 2006/0036206 | February 2006 | Yokoyama et al. |

SUMMARY OF THE INVENTION

A nasal pack according to the present invention is cylindrical in shape and is suitable for a patient's self application in controlling epistaxis. The pack has a widget comprised of compressed cotton or cellulosic fiber. The term "widget" is used in this application to refer to a pack dimensioned and configured to fit within the human nasal cavity. The widget is extended just past the opening of the nostril providing a place on which to grip the pack also allowing containment and prevent contact of blood when disposing of pack. The widget is placed within the nasal cavity upon occurrence of a nosebleed thereby absorbing blood and at the same time applying constant pressure to the nasal wall to assist in the coagulation process stopping the nosebleed. When the nosebleed is ended, the pack may be removed by applying a gentle pulling force to the bottom of the nose pack. Blood clots will naturally expel at time of removal clearing the nasal sinuses.

Accordingly, it is a principal object of the invention to provide simple, ready to use, effective treatment for epistaxis which can be applied and removed without assistance designed to conceal the problem of a nosebleed.

An additional object of the invention is to provide a treatment for epistaxis in which constant, continued pressure is applied to the nostril assisting in stopping the nosebleed.

A further object of the invention is to provide convenience of a nosebleed treatment that is easy to transport and conceal.

It is an object of the invention to provide improved elements and arrangements thereof in an apparatus for the purposes described which is reliable, disposable, inexpensive and fully effective in accomplishing its intended purposes.

These and other obvious objects of the present invention will become apparent upon further review of the following specification and drawings.

BRIEF DESCRIPTION OF THE DRAWINGS

FIG. 1 is a perspective view of the completed nose pack positioned to be inserted into the inside of a nostril.

FIG. 2A is a side view of an elongate body comprising compressed absorbent cotton formed into a cylindrical shape with a rounded tip at one end according to a first embodiment.

FIG. 2B is a side view of an elongate body comprising compressed absorbent cotton formed into a cylindrical shape with rounded tips at both ends according to a second embodiment.

FIG. 3 is a side view of a clear or colored plastic coating or sleeve for covering the lower portion and lower end of the elongate body shown in FIG. 2A.

FIG. 4 is a side view of the nose pack completed and ready to package, with the upper portion and rounded tip covered by a lubricant or medication.

DETAILED DESCRIPTION OF INVENTION

A nose pack 10 for controlling epistaxis according to the present invention will be explained in detail with reference to FIGS. 1 to 4 of the accompanying drawings.

The nose pack 10 includes an elongate body 1 comprising compressed absorbent cotton formed into a cylindrical shape with a rounded upper end 11. The cylindrical shape has an upper portion 12 adjacent to the rounded upper end 11, and a lower portion 13. The rounded upper end 11 and the upper portion 12 of the elongate body 1 are dimensioned and configured to fit into a nostril 2.

The elongate body 1 has a lower end 14 opposite to the rounded upper end 11. The lower portion 13 and the lower end 14 of the elongate body 1 are covered by a plastic coating or plastic sleeve 3. The plastic coating or plastic sleeve 3 is arranged to contain blood within the absorbent cotton of the elongate body 1 and to provide a place to grip the pack 10 without contacting blood absorbed by the absorbent cotton.

An alternative embodiment of an elongate body 5 for the nose pack 10 of the present invention is illustrated in FIG. 2B. The elongate body 5 of this embodiment has a rounded upper end 11' and a rounded lower end 14'.

The plastic coating or plastic sleeve 3 can be colored to conceal blood absorbed into the lower portion 13 of the elongate body 1 during use. The plastic coating or plastic sleeve 3 can be permanently attached and sealed to the lower portion 13 of the elongate body 1.

As illustrated in FIG. 4, the upper portion 12 and rounded upper end 11 can be prelubricated with a lubricant 4 for lubricating a nasal wall during use, or premedicated with a medication 4 for applying medicine to a nasal wall during use. The nose pack 10 can be used as an applicator to apply lubricants to relieve dry nasal walls to prevent recurring nosebleeds. The nose pack 10 can also be used as a new and effective method for delivering medications into the blood system.

I claim:

1. A nose pack for controlling epistaxis, consisting of:
   an elongate body comprising compressed absorbent cotton, and
   a plastic coating or plastic sleeve covering a portion of said elongate body;
   said compressed absorbent cotton being formed into a cylindrical shape with a rounded upper end, said cylindrical shape having an upper portion adjacent to said rounded upper end and a lower portion, said rounded upper end and said upper portion of said elongate body being dimensioned and configured to provide a means for fitting into a human nostril and applying a constant pressure to a nasal wall of the nostril;
   said elongate body comprising a lower end opposite to said rounded upper end, said lower portion and said lower end of said elongate body being covered and sealed by said plastic coating or plastic sleeve to contain blood within said absorbent cotton and to provide a place to grip the pack without contacting blood absorbed by said absorbent cotton;
   wherein said plastic coating or plastic sleeve closely conforms to the lower portion and lower end of the elongate body so as not to protrude substantially beyond the cylindrical shape of said elongate body.

2. The nose pack according to claim 1, wherein said upper portion is prelubricated for lubricating a nasal wall during use.

3. The nose pack according to claim 1, wherein said upper portion of the elongate body is premedicated for applying medicine to a nasal wall during use.

4. The nose pack according to claim 1, wherein said lower end of said elongate body is rounded.

5. The nose pack according to claim 1, wherein said plastic coating or plastic sleeve is colored to conceal blood absorbed into the lower portion of said elongate body during use.

6. The nose pack according to claim 1, wherein said plastic coating or plastic sleeve is permanently attached and sealed to the lower portion of said elongate body.

7. The nose pack according to claim 1, wherein said lower end of the elongate body extends just below an opening of the nostril during use.

* * * * *